(12) United States Patent
Sahoo

(10) Patent No.: US 9,084,655 B2
(45) Date of Patent: *Jul. 21, 2015

(54) ADJUSTABLE FLOSSING MOUTHPIECE

(76) Inventor: Rakesh Joshua Sahoo, Sugar Land, TX (US)

(*) Notice: Subject to any disclaimer, the term of this patent is extended or adjusted under 35 U.S.C. 154(b) by 181 days.

This patent is subject to a terminal disclaimer.

(21) Appl. No.: 13/403,542

(22) Filed: Feb. 23, 2012

(65) Prior Publication Data

US 2013/0220356 A1   Aug. 29, 2013

Related U.S. Application Data

(63) Continuation-in-part of application No. 13/329,084, filed on Dec. 16, 2011, now Pat. No. 8,936,031.

(60) Provisional application No. 61/424,626, filed on Dec. 18, 2010.

(51) Int. Cl.
*A61C 15/00* (2006.01)
*A61C 15/04* (2006.01)
*A61C 17/22* (2006.01)

(52) U.S. Cl.
CPC .............. *A61C 15/042* (2013.01); *A61C 15/046* (2013.01); *A61C 15/048* (2013.01); *A61C 17/228* (2013.01)

(58) Field of Classification Search
CPC .... A61C 15/04; A61C 15/042; A61C 15/045; A61C 15/046; A61C 15/047; A61C 15/00; A61C 15/043; A61C 15/02; A61C 15/048
USPC ............ 132/323–329, 321; 433/141, 216, 37; 601/164
See application file for complete search history.

(56) References Cited

U.S. PATENT DOCUMENTS

| | | | | |
|---|---|---|---|---|
| 3,335,718 A * | 8/1967 | Sexton | .......................... | 601/139 |
| 5,022,417 A * | 6/1991 | Cimini | .......................... | 132/323 |
| 5,190,062 A * | 3/1993 | Rafaeli | .......................... | 132/323 |
| 5,429,145 A * | 7/1995 | Bral | .............................. | 132/323 |
| 7,220,123 B1 * | 5/2007 | Karapetyan | ..................... | 433/37 |
| 7,537,451 B1 * | 5/2009 | Ramnarine | .................... | 433/216 |
| 2005/0133057 A1 * | 6/2005 | Kirstein | ........................ | 132/323 |
| 2006/0014121 A1 * | 1/2006 | DelGrosso | .................... | 433/216 |

* cited by examiner

*Primary Examiner* — Robyn Doan
(74) *Attorney, Agent, or Firm* — John K. Buche; Scott Compton; Buche & Associates, P.C.

(57) ABSTRACT

A method and device for flossing teeth utilizing positionally adjustable floss picks holding strands of dental floss. The floss picks fit into a retainer component and are positioned to insert the floss strands into the interproximal dental spaces between the user's teeth. The position of individual floss picks can be adjusted to achieve the correct fit. The disclosure also teaches a retainer with two sides comprising slotted tracks extending substantially the length of each retainer side. The slots contain floss strands.

20 Claims, 36 Drawing Sheets

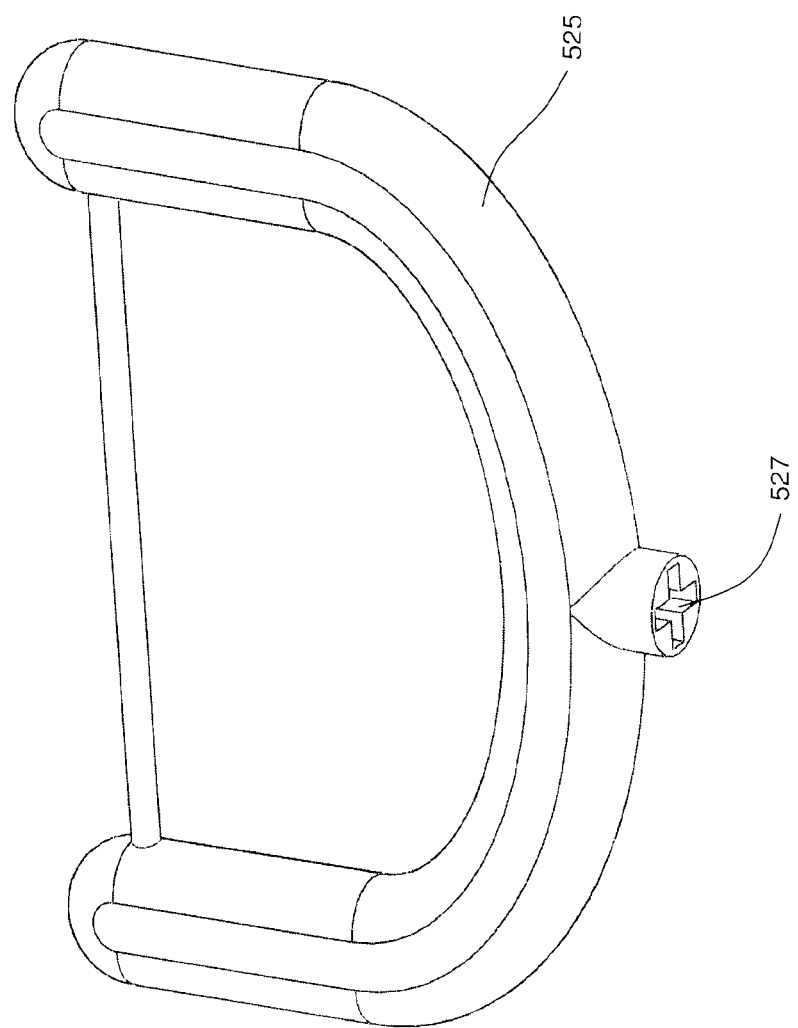

ADJUSTABLE FLOSSING MOUTHPIECE

RELATED APPLICATIONS

This application is a Continuation In Part of application Ser. No. 13/329,084 filed Dec. 16, 2011 which is incorporated by reference herein in its entirety. This application also claims priority to and incorporates by reference herein the provisional application Ser. No. 61/424,626 filed Dec. 18, 2010 entitled "Adjustable Flossing Mouthpiece Patent Inquiry".

1. FIELD OF USE

This disclosure pertains to an improved method of cleaning teeth and maintaining dental health.

2. RELATED ART

Tooth brushes, dental floss and related holder apparatus are known in the art.

SUMMARY OF INVENTION

This disclosure pertains to one or more retainer devices holding floss picks wherein the floss picks are adjustable relative to the interproximal spaces between the teeth. The disclosure also illustrates a retainer device which incorporates a dual opposing track component that holds slideable floss strands. As used herein, floss may be fibrous strands (waxed or unwaxed, woven or unwoven, or braided) used to clean the interproximal spaces between teeth. Floss may comprise one or more loops or bristles.

SUMMARY OF DRAWINGS

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

FIG. 4b illustrates the retainer and floss pick oriented to fit with the teeth of the lower jaw. Protrusions illustrated on the retainer of FIG. 4b can fit together with complementary indentations in the retainer of FIG. 4a.

FIG. 12a illustrates a perspective view of the upper portion of a floss pick with connective holder detachable/attachable to the base.

DETAILED DESCRIPTION OF THE DISCLOSURE

Figure 1A:
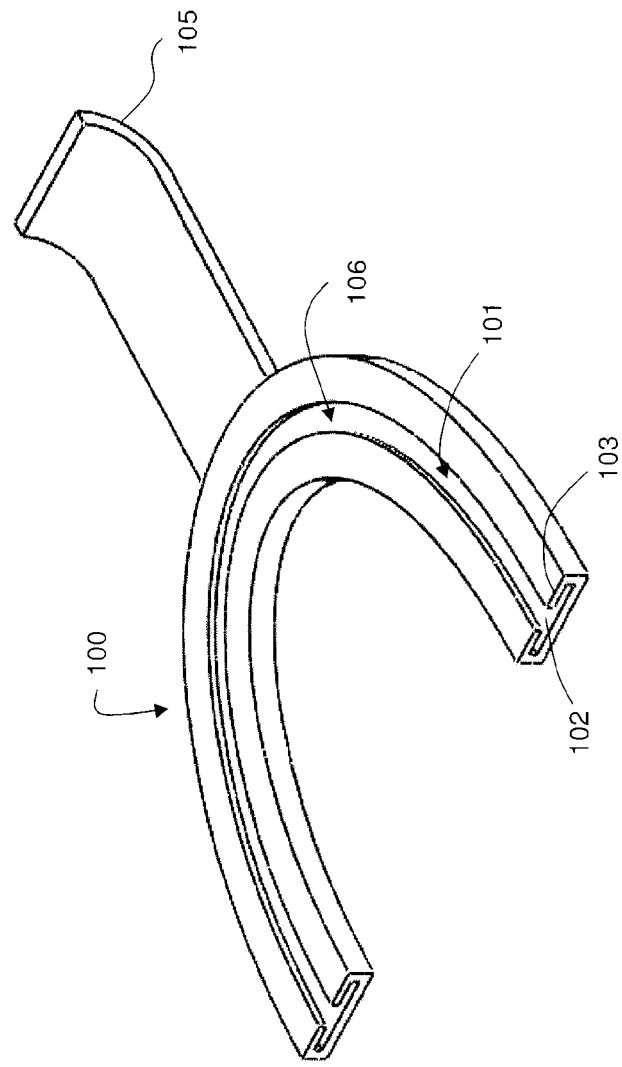
FIG. 1a illustrates a perspective view of a retainer component with a handle. Also illustrated is a channel subcomponent that can be used to hold a floss pick component.

The device subject of this disclosure facilitates dental hygiene. One of the most important activities promoting good dental hygiene is flossing. This activity requires pulling or pushing a strand of dental floss between each tooth, i.e., in the interproximal dental space. The floss is rubbed against the side surface of each tooth and under the gum line. The activity cleans food particles and debris situated between the teeth and below the gum line. Flossing the teeth at the rear of the mouth by prior art methods are often performed with considerable difficulty.

The device subject of this disclosure simplifies the flossing activity. It also makes the activity more efficient. The device can comprise a lower jaw retainer or component and an upper jaw retainer or component. In another embodiment, the device comprises a single retainer component for both the upper and lower jaw.

Positioned on each retainer are floss picks aligned with the interproximal dental spaces between the teeth. The floss picks hold strands of floss that may also comprise bristles and hoops. The user places the device in his or her mouth and closes his or her jaws on the device, thereby inserting floss between the teeth. The floss is held by the floss picks. The user can move individual floss picks on the retainer to match the position of the floss pick with the interproximal dental spacing. This is referred to as positionally moveable in the retainer. This can require removal of the device from the user's mouth. It may also require pressing on the friction held floss picks to move the floss pick within the retainer. In another embodiment, the floss pick can be moved by movement of the floss pick base along the serrated edge of the retainer channel shoulder. Other mechanisms for moving and positioning the floss picks within the retainer will be apparent to persons skilled in the art and are subject of this disclosure.

The floss can be rubbed on the teeth surfaces by gently moving the mouthpiece back and forth and side to side and opening and closing the mouth. The device also allows the user to adjust the position of individual floss picks. It will be appreciated that once a comfortable or effective cleaning position is achieved for each floss pick, the floss pick stays in that position. The user can purchase the device with floss picks preassembled according to the average interproximal dental spacing for an adult or a child. Final adjustments can be made by the user. It is not necessary to have the device adjusted or fitted by a dental hygienist.

In one embodiment, the device comprises a retainer component ("retainer") that contains an arch or curved structure that matches the dental arch of an individual, i.e. the pattern of the teeth of the upper jaw and lower jaw. The retainer, having a generally U shape, contains a channel following the outline of the U shape. Adjacent to the channel are two shoulders. As will be explained below, the shoulders may have a serrated surface. The retainer also has a flat bottom surface. The retainer may also have a handle that protrudes from the user's mouth. This can assist in maneuvering the retainer and floss picks into correct positions relative to the interproximal spaces. The handle can also maneuver the floss picks between the front and back dental surfaces of the interproximal spaces and beneath the gum line during use.

It will be appreciated that the retainer may comprise two separate components, i.e., an upper retainer and a lower retainer. The lower retainer will be oriented to the teeth of the lower jaw. Accordingly, the channel described above will also be oriented to the teeth of the lower jaw and the flat surface of the lower retainer will abut the flat surface of the upper retainer. In another embodiment discussed below, there may be a single retainer with an upper and lower channel. The single retainer may comprise two components and one component can slide laterally relative to the other component.

The retainer holds floss picks. In one embodiment, the floss picks comprise a base. The base fits into the channel of the retainer. In one embodiment, friction between the base and the retainer channel controls or maintains the position of the floss pick in the retainer. Part or all of the floss pick base and the channel and shoulders can be covered in a friction material. Pads that interface with the shoulder structure of the retainer may comprise these materials. Examples of friction material include but are not limited to textured rubber, polyurethane, or ethylene vinyl acetate.

Extending from the base of the floss pick is a neck. The neck may join a U shaped component. The U shaped component comprises arms. The U shaped component holds a strand of dental floss. The floss can be held by holes in the U shaped component. The holes will be proximate to the end of the two arms of the U shaped component. In another embodiment, the arms may contain slots for holding the floss. In another embodiment, the slots may include a cutting surface to allow the user to easily control the amount of floss placed between the arms of the U shaped component of the floss pick. This can allow the user to replace the strands of dental floss. In yet another embodiment, the floss may be molded to the ends of the floss pick arms. In one embodiment, the floss is held taut between the U shaped arms. In another embodiment the floss may have a predetermined slack between the arms. In another embodiment, the floss may be elastic or compliant. In yet another embodiment the floss is inelastic or noncompliant.

In one embodiment, the floss picks positioned at the dental arch may comprise wider U shaped components or arms holding a greater length of floss. This greater length may compensate for an overbite of the user. In another embodiment, the floss pick may be positioned at an angle other than normal to the axis of the retainer channel. This will allow the user to adjust the device for irregular positioned teeth.

The height or width of the floss picks may vary, depending upon the position of the floss pick on the retainer. Floss picks position at the back of the mouth may be smaller since the back of the jaw does not open as wide as the front. This may facilitate placement of the floss pick retainer device in the user's mouth. The shorter floss picks, understood to protrude above the retainer, fit more comfortably in the area of the back of the jaw. Floss picks positioned proximate to the canine teeth may be taller and narrower.

It will be appreciated that the interproximal dental spaces are located approximately in the same place for all individuals. In one embodiment, upper and lower retainers can be furnished with floss picks positioned in the retainer channel at the approximate location of each interproximal dental space. The user can separately position the floss picks of each retainer, including by placing the upper and lower retainers separately in the mouth, positioning the floss picks appropriately, reattaching the upper and lower retainers, and placing the combined device in the user's mouth. In one embodiment, each retainer can be separately placed in the user's mouth. The two-part retainer (upper and lower retainer) can be detachably attached. In one embodiment, the attachment mechanisms are complementary protrusions and indentations on the bottom of each retainer component. The user can adjust the positioning of each floss pick as necessary in the retainer to match the spacing to of the interproximal spacing between the user's teeth. As stated above, the floss picks are positionally moveable in the retainer. This may involve removing the device from the user's mouth and the user adjusting the position of one or more floss picks with his or her fingers.

In one embodiment, the retainer is made of a compliant material. The elasticity of this compliant material may provide the mechanism to hold the floss pick in place on the retainer.

In one embodiment, the floss picks are moved in the channel subcomponent of the retainer. In one embodiment, the individual floss picks may be fixedly positioned in the retainer channel so that the position of the floss picks will not change through flossing action. In one embodiment, the base of the floss pick fits between the shoulders of the retainer channel. The base of the floss pick may have ends dimensioned to fit between protrusions or serrations on the shoulders of the retainer channel. The retainer and/or floss pick structure can be made of a plastic material sufficiently compliant to allow the ends of the floss pick base to be moved across the protrusions of the retainer channel shoulders.

In one embodiment, there is an upper jaw retainer and a lower jaw retainer. The bottom surface of the upper jaw retainer and the upper surface of the lower jaw retainer can have complementary protrusions and indentations allowing the separate retainers to fit together in the mouth. In another embodiment the protrusion of one retainer fits into a slot in the second retainer thereby facilitating lateral movement of each retainer relative to the other. This may facilitate accommodating a user's overbite.

In another embodiment, the retainer can be cylindrically shaped and bent or molded in a U shape to match the dental arch. The retainer can also have a cross-section in the shape of a square or any other shape. The cross section selected can match the inner dimension of the floss pick base. The floss pick can slide along the outer surface of the retainer. Stated differently, if the retainer has a circular cross section, the floss pick base will have a circular aperture dimensioned to fit onto the retainer.

It will be appreciated that the structure of the floss pick can be modified so that an upper and lower jaw floss pick can be joined to share a single base. The base, as explained in the preceding paragraph, comprises an aperture that fits over the retainer. It will be appreciated that the retainer can have a serrated edge that matches one or more protrusions on the inside surface of the floss pick base aperture. Thus the position of the floss pick upon the retainer can be adjusted and controlled. In another embodiment, the position of the floss pick in the retainer is controlled by friction between the floss pick base and the retainer channel holding the base. In another embodiment, the position of the floss pick is controlled by the interaction between the floss pick base and the compliant material of the retainer. This can include the cylindrically shaped retainer discussed above with the floss picks utilizing complementary sized apertures.

Figure 1B:
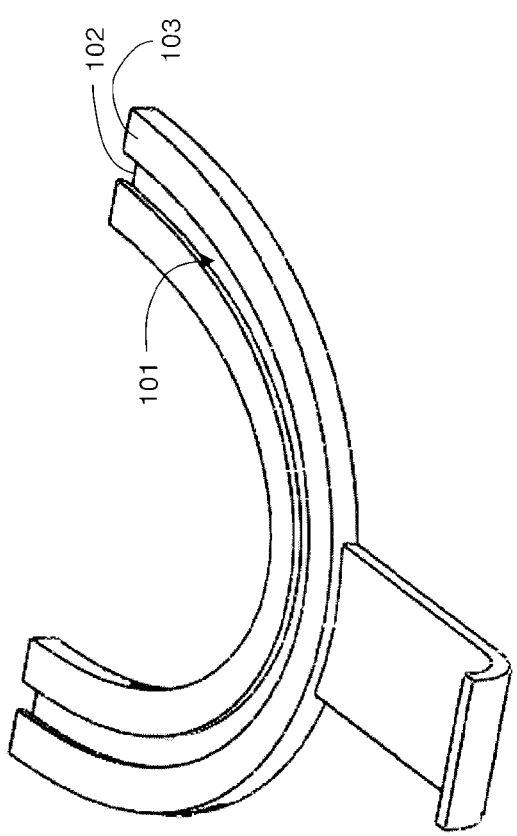
FIG. 1b illustrates another perspective view of the retainer component.

FIG. 1a illustrates one embodiment of the device. Illustrated is the U shaped retainer 100. Also shown is the handle 105 that may protrude from the user's mouth. The retainer comprises a channel 101 that follows the dental arch 106. The channel contains a flat bottom 102 and two shoulders 103. FIG. 1b illustrates another perspective of the retainer including the channel 101, bottom surface 102 and shoulders 103. It will be appreciated that the openings at the end of the retainer and illustrating the channel may be closed.

Figure 2A:
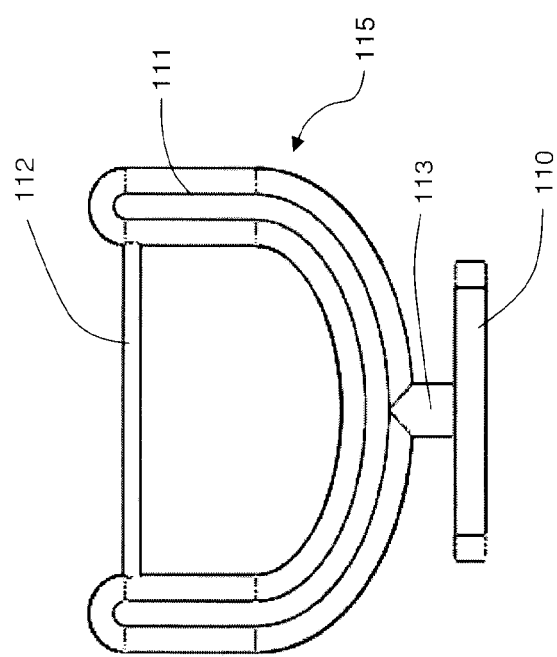
FIG. 2a illustrates a front view of a floss pick including the moveable holder component that fits within the channel subcomponent of the retainer.
Figure 2B:
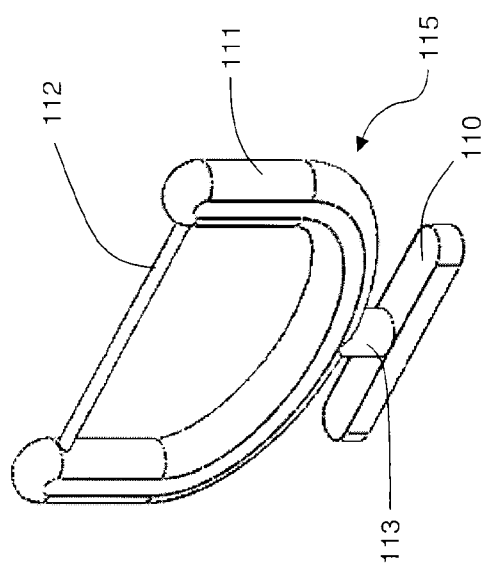
FIG. 2b illustrates a perspective view of a floss pick component showing the floss strand and the moveable holder component.
Figure 2C:
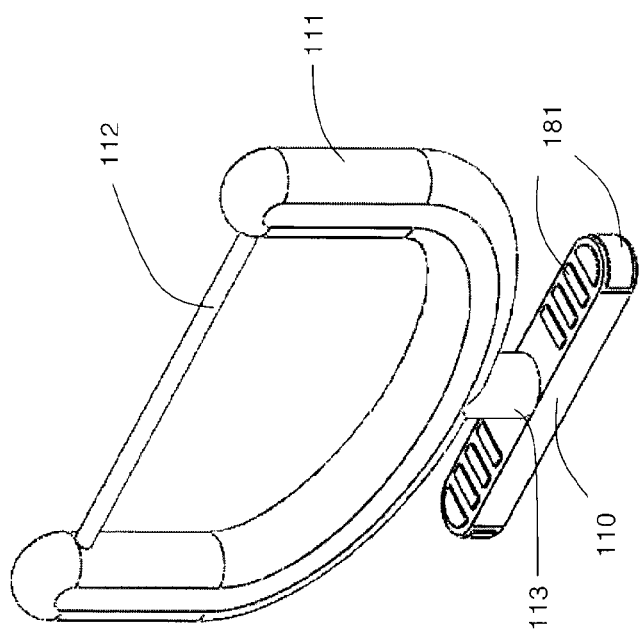
FIG. 2c illustrates a prospective view of the floss pick containing friction pads which may be used to moveably position the floss pick in the retainer.

FIG. 2a illustrates a side view of floss pick 115. Included is the base 110, neck 113 connecting the base and the U shaped arms 111 holding the floss 112. It will be appreciated that the flat base of the floss pick fits/slides onto the flat surface 102 of the retainer. It will be appreciated that in some embodiments the base may not be flat. For example the bottom may be rounded to conform to an undulating surface of the channel. This may facilitate floss pick position control. The retainer shoulders 103 fit over the top of the base 110 and the neck 113 extends through the opening of the channel 101. FIG. 2b is a perspective of the floss pick 115. FIG. 2c illustrates a perspective view of the base 110 further comprising friction material 181 to facilitate holding the base in a fixed position in the retainer. The friction pads 181 may interface with the surfaces of the retainer shoulders, which may also comprise friction material.

Figure 3A:
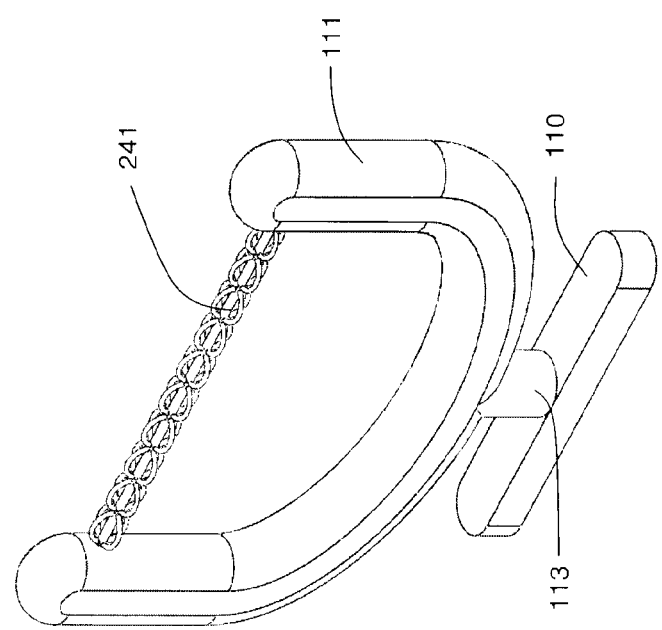
FIG. 3a illustrates a perspective view of a floss pick containing a hooped floss strand.

FIG. 3a is a perspective view of the floss pick 115, including the base 110, neck 113, U shaped arms 111 and floss strand comprising hoops 241. The hoop structure increases the effective diameter of the floss to improve cleaning action within the interproximal dental space. In one embodiment, the hoop may be fabricated from floss woven in a circular shape. In another embodiment the floss pick is extruded or injection molded to include a softer portion forming a floss hoop. In other embodiments, the strand may contain bristles.

Figure 13:
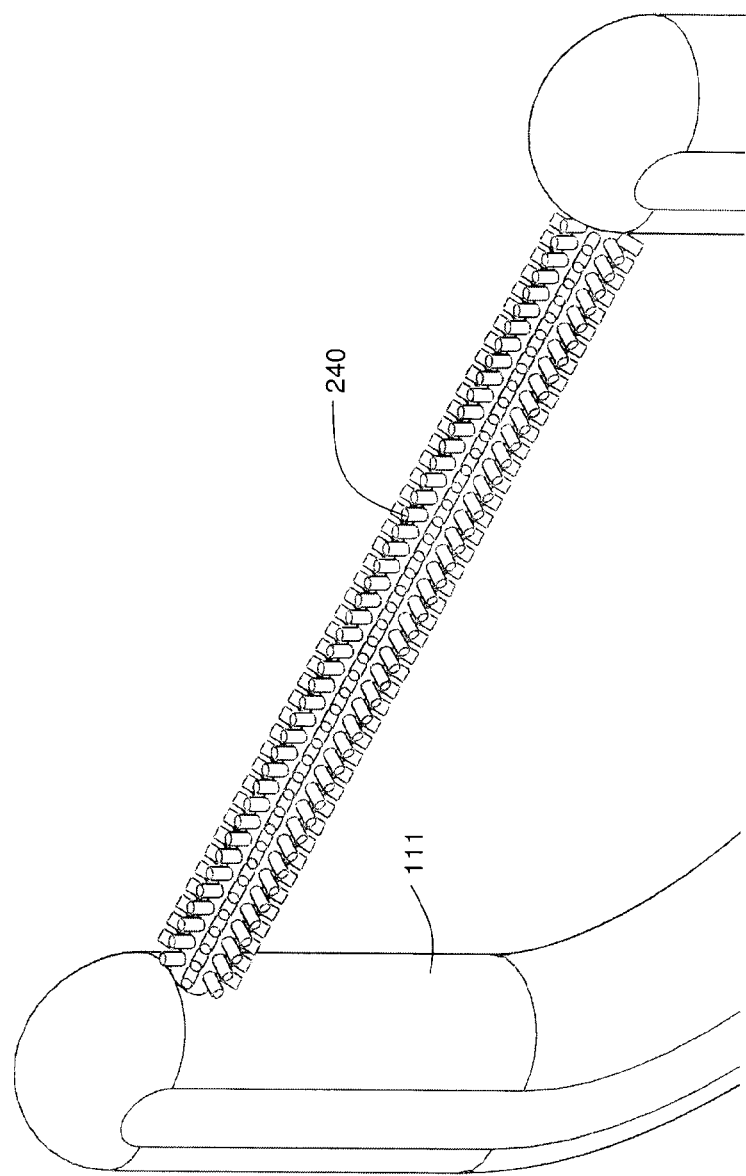
FIG. 13 is a perspective view of a floss pick adapted to include bristles.

FIG. 13 illustrates another embodiment of the floss pick wherein the floss pick comprises bristles 240. Also illustrated is the U shaped arms 111

Figure 3B:
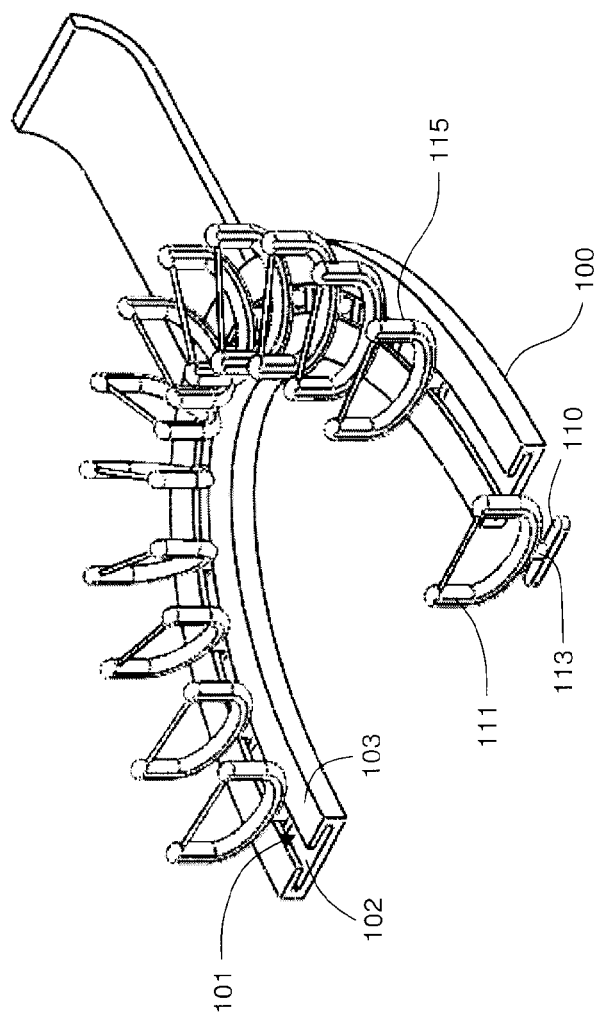
FIG. 3b illustrates a perspective view of a plurality of floss picks adjustably positioned in the channel subcomponent of the retainer.

It will be appreciated that the floss pick may not have U shaped arms. For example, but not by way of limitation, the floss pick arms may have a Y shape. Other configurations are possible and will be apparent to persons skilled in the art. Such configurations are included within the scope of this disclosure. FIG. 3b illustrates a plurality of floss picks 115 positioned in the U shaped retainer 100. Illustrated is the floss pick base 110, neck 113, and U shaped arms 111. Also illustrated is the retainer channel 101, flat channel bottom surface 102 and shoulders 103. It will be appreciated that the flat bottom 113 of the floss pick 115 slides on the flat bottom surface 102 of the channel and the neck 113 protrudes between the shoulders 103 of the channel 101.

Figure 4A:
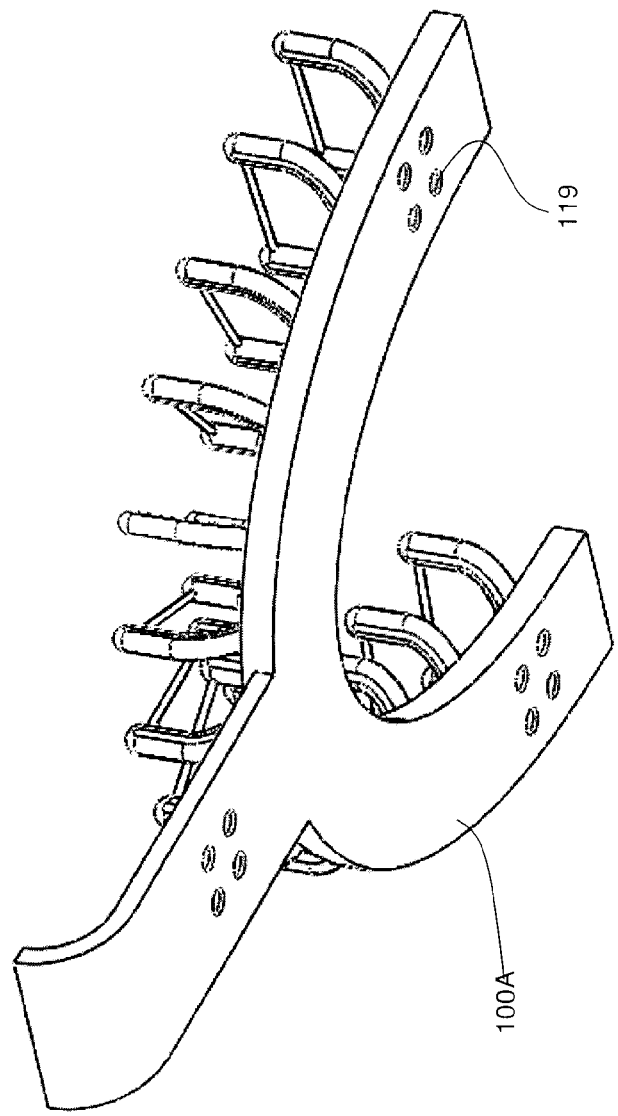
FIG. 4a illustrates the retainer and floss picks oriented to fit with the teeth of the upper jaw.
Figure 4B:
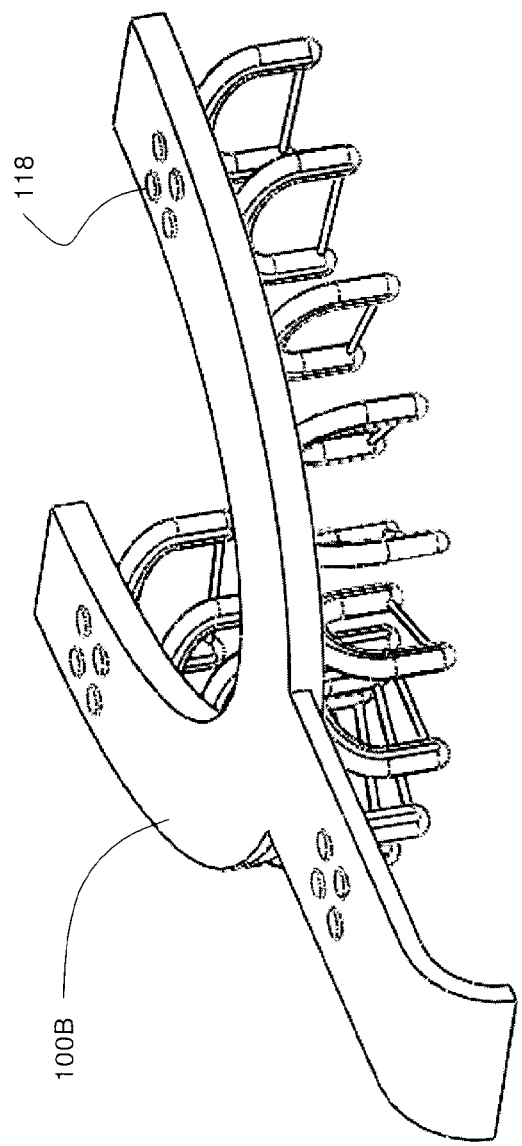

FIG. 4a illustrates a bottom perspective view of the upper jaw retainer 100A. Also illustrated are indentations 119. FIG. 4b illustrates a top perspective view of a lower jaw retainer 110B with complementary protrusions 118 matching the indentations 119 of 100A. These complementary indentations and protrusions fit together and allow both retainers to move in the mouth as a single unit.

Figure 5A:
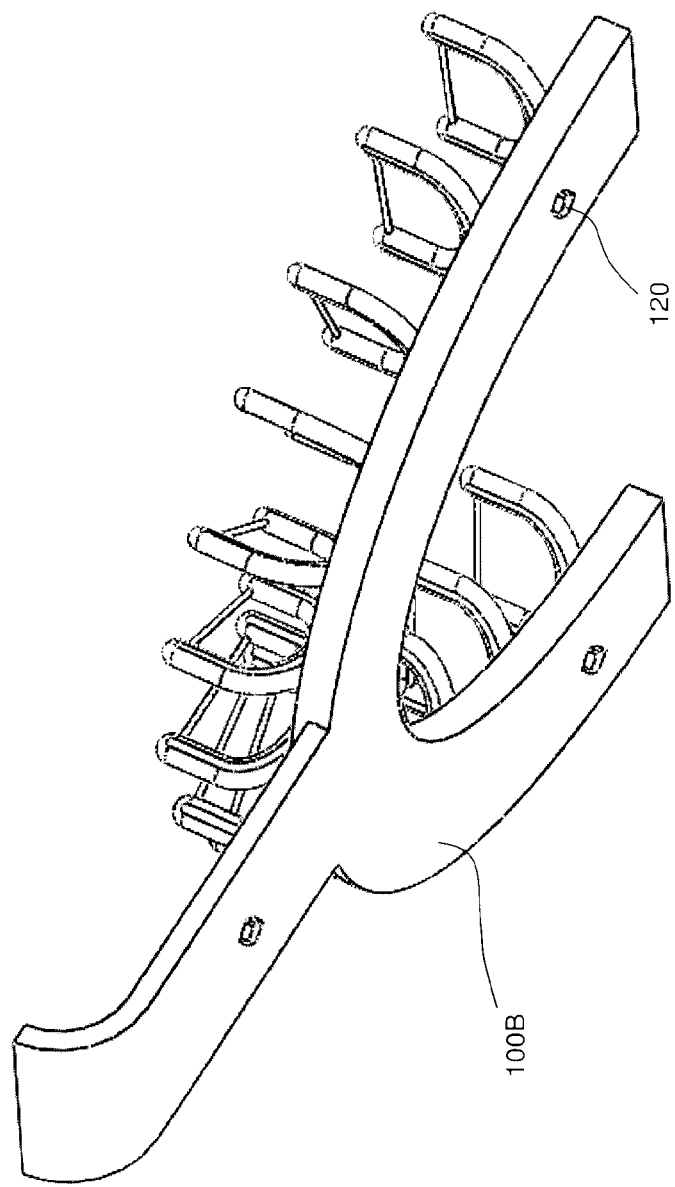
FIGS. 5a and 5b illustrate another perspective of the upper and lower retainers. These retainers also contain complementary slots and protrusions to allow movement of each retainer.
Figure 5B:
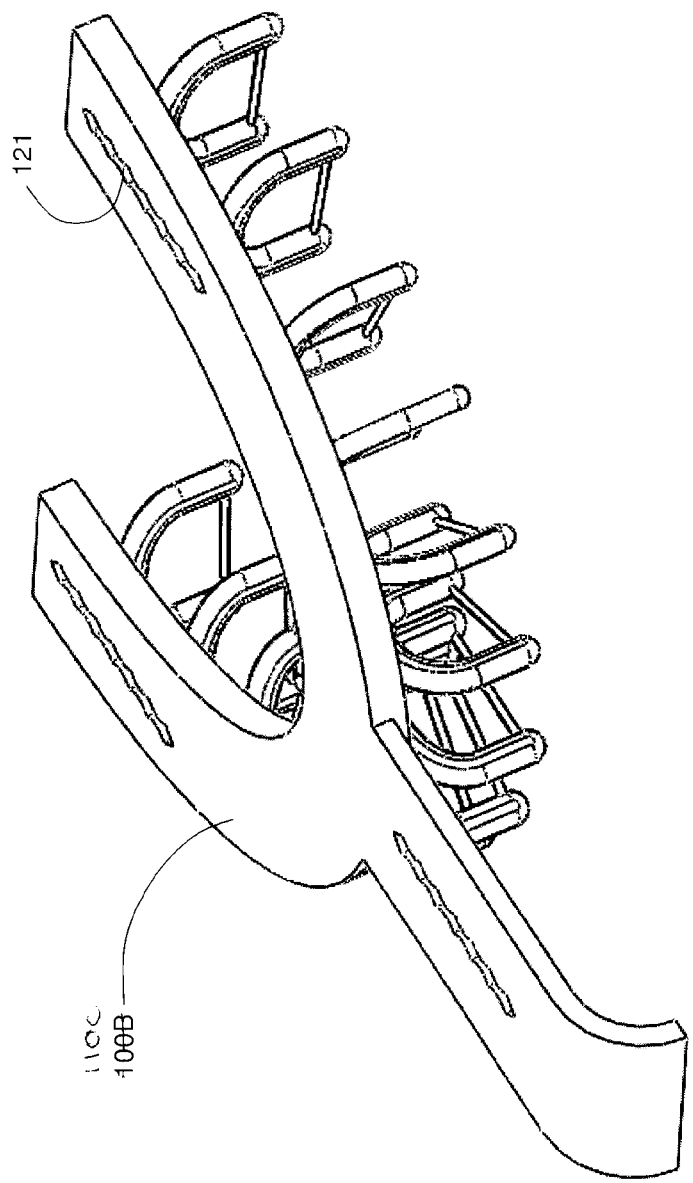
Figure 6:
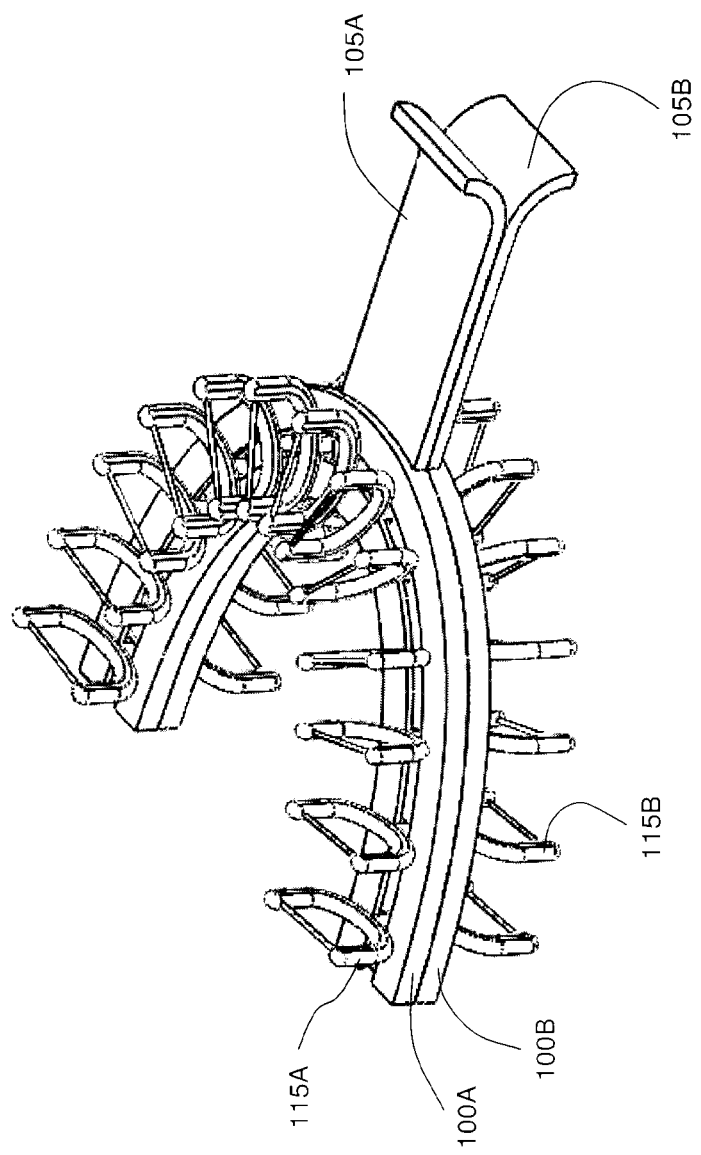
FIG. 6 is a perspective illustration of the upper and lower retainers and floss picks as they may be inserted into the mouth.

FIG. 5a illustrates another embodiment of the upper jaw retainer 100B with protrusions 120. These protrusions slideably fit into grooves 121 illustrated in the lower jaw retainer 100B in FIG. 5b. The grooves may be straight or serrated as illustrated in FIG. 5b. FIG. 6 illustrates the upper jaw retainer 100A and lower jaw retainer 100B with the corresponding and oppositely oriented floss picks 115A, 115B. The handles 105A and 105B are also illustrated.

Figure 7:
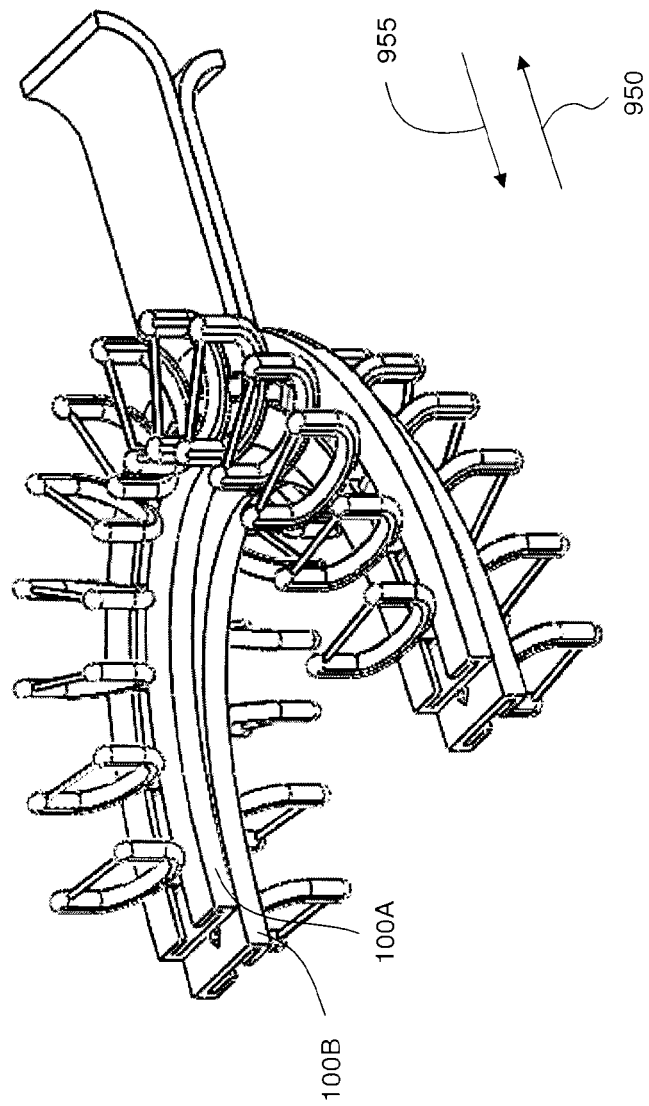
FIG. 7 illustrates that the upper and lower retainer may be moved independently of the other.

FIG. 7 illustrates the embodiment illustrated in FIG. 6. Illustrated is the movement of the two retainers 100A, 100B as depicted by vector arrows 950, 955.

In another embodiment, not shown, the retainer for the upper and lower jaw can be a single unit with a top and bottom channel for retaining and positioning the floss picks. In yet another embodiment, the single retainer can permit the upper jaw retainer component to laterally move in relation to the attached lower jaw component.

Figure 8:
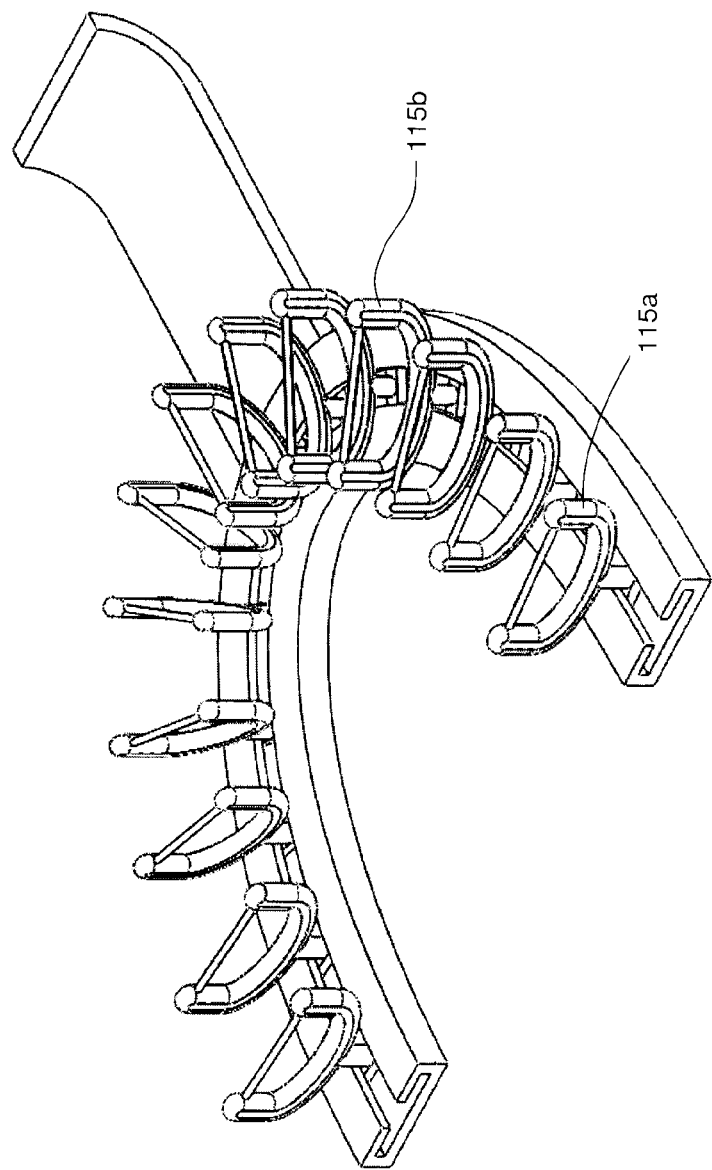
FIG. 8 illustrates that the floss picks positioned for use with the back or rear teeth can be shorter than the floss picks used for the front teeth.

FIG. 8 illustrates the retainer device containing floss picks of varying heights. For example the floss picks 115a may be shorter than floss picks positioned at 115b. This may facilitate placement of the floss pick retainer device in the user's mouth. The shorter floss picks, understood to protrude above the retainer, fit more comfortably in the area of the back of the jaw. It will be appreciated that the back of the jaw does not open as widely as the front of the jaw.

Figure 9:
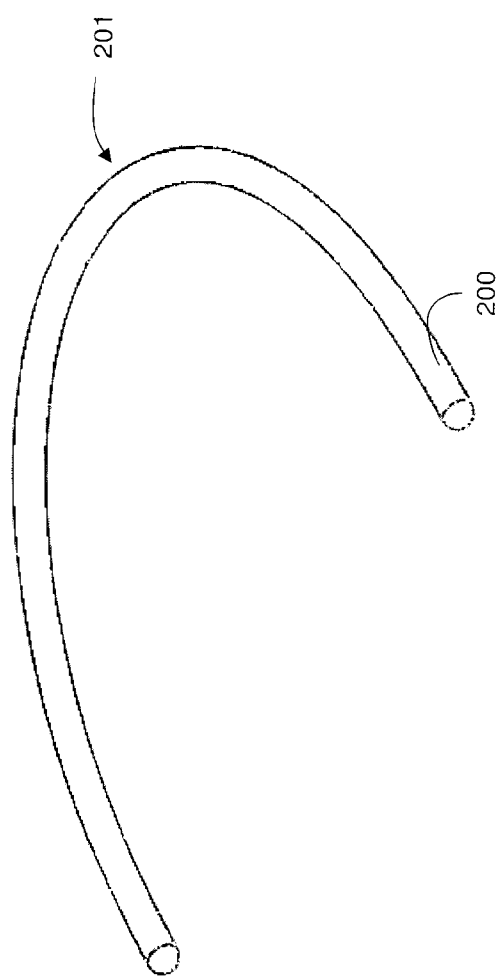
FIG. 9 is a perspective view of another embodiment of a retainer component.
Figure 10A:
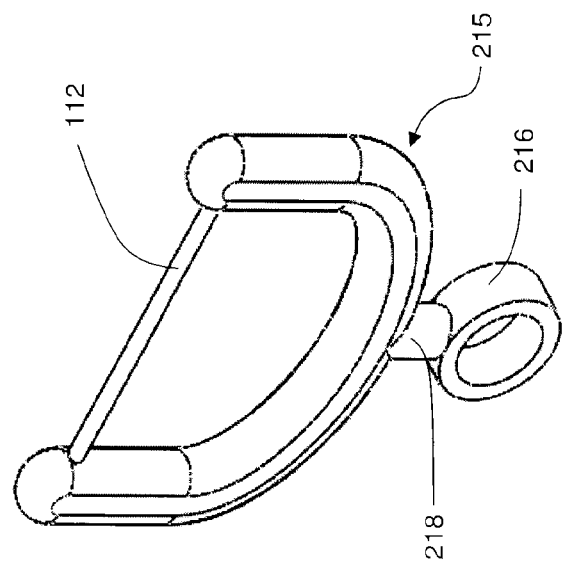
FIG. 10a illustrates a perspective view of a floss pick adapted to the retainer of FIG. 9.
Figure 10B:
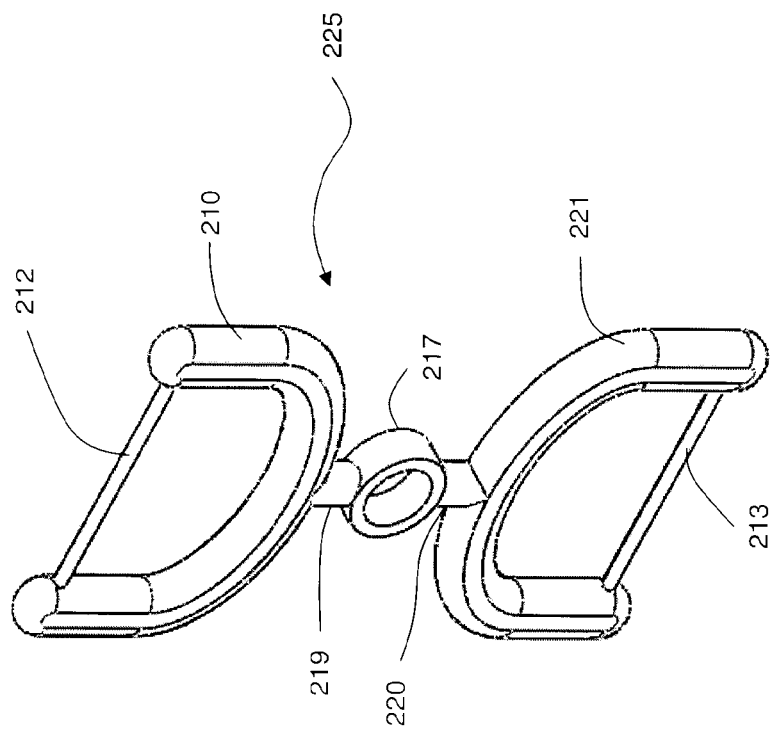
FIG. 10b illustrates a perspective view of an alternate embodiment of a floss pick capable of holding a floss strand for the teeth of both the upper and lower jaw.

FIG. 9 illustrates another embodiment of the retainer component 200 including the curvature to match the dental arch 201. Here the retainer has a cylindrical shape. FIG. 10a illustrates a floss pick 215 adapted to fit on the cylindrical shaped retainer. The floss pick has a round base 216 with an aperture, a neck 218, and U shaped arms holding floss 112. FIG. 10b illustrates a modified floss pick 225 comprising upper and lower floss picks with opposing arms 210, 221

Figure 11A:
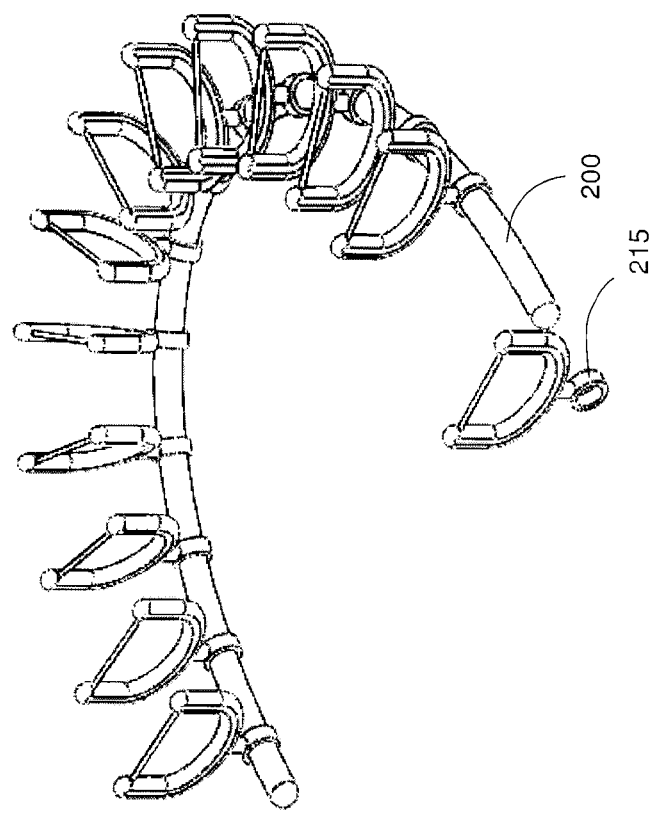
FIG. 11a illustrates a perspective view of a plurality of floss pick holders on the retainer.
Figure 11B:
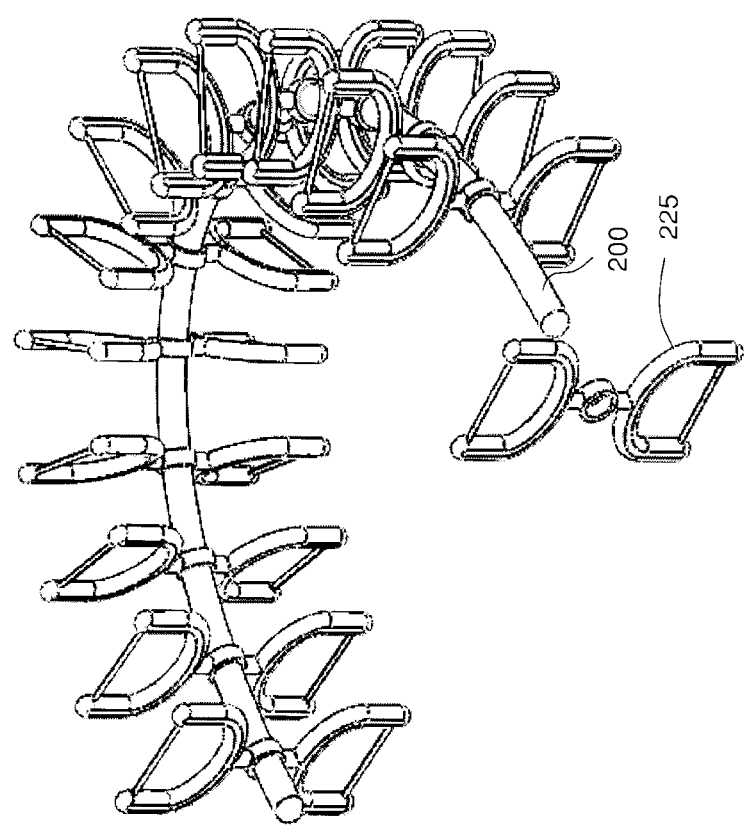
FIG. 11b illustrates a plurality of floss pick holders for both the upper and lower jaw on the retainer.

FIG. 11a illustrates an embodiment of the invention where a plurality of floss picks 215 are mounted on the cylindrical retainer 200. FIG. 11b illustrates the device wherein the each floss pick 225 is modified to be oriented to both the teeth of the lower and upper jaw. Each floss pick is mounted on the cylindrical retainer 200.

FIG. 10b also illustrates the floss pick embodiment wherein the floss pick 225 is modified to be oriented to the lower jaw and upper jaw. It will be appreciated that only a single retainer component is required. See FIG. 11b. Illustrated is the retainer base 217 comprising an aperture with an outer diameter complementary to the diameter of the cylindrical retainer, the opposing supporting neck structures 219, 220, U shaped arms 210, 221 and floss strands 212, 213.

Figure 12B:
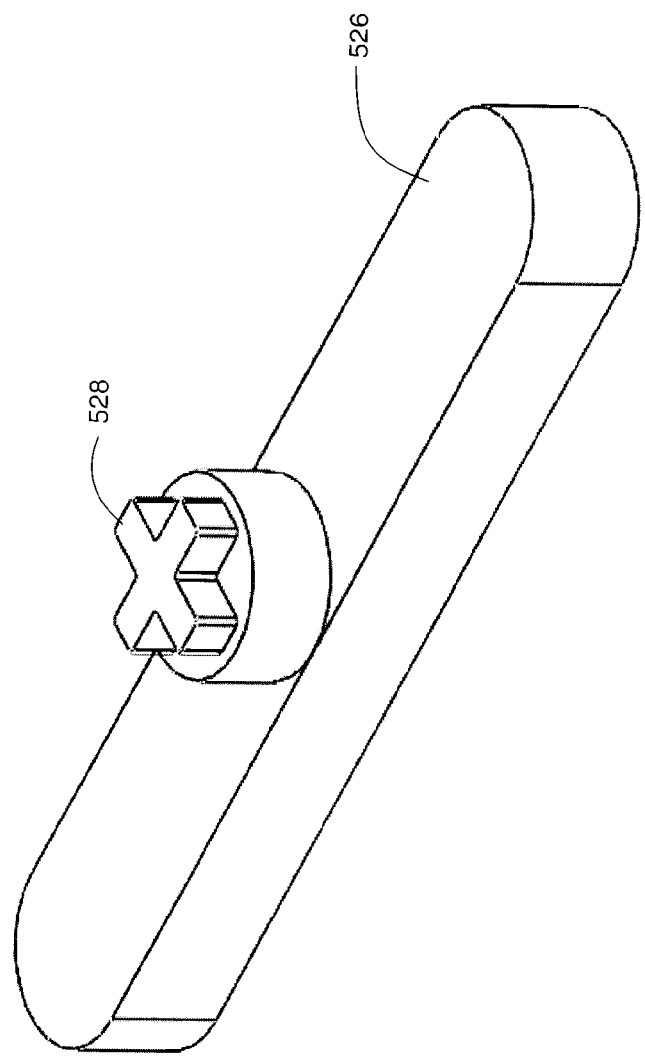
FIG. 12b illustrates the base of a floss pick with complementary connective coupling for the upper portion of the floss pick.

One embodiment of the device includes a snap-on replaceable floss pick head. FIG. 12a is a detachable floss pick head 525 that is removable from the base 526 (FIG. 12b). The floss pick head can be attached to the base. The floss pick head is comprised of a multi surfaced female connector 527. The floss pick base comprises a multi surfaced male connector 528. FIG. 12b. The detachable head and base may also comprise single cylindrical male and female connectors. It will be appreciated that other configurations or mechanisms are included within the scope of the disclosure.

Figure 14:
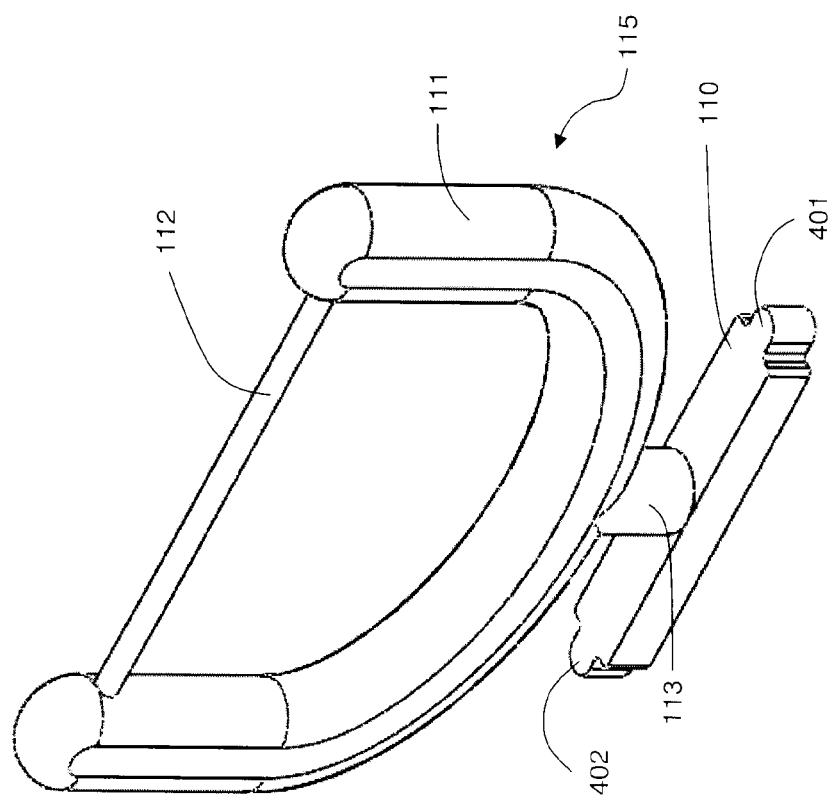
FIG. 14 illustrates a floss pick with a grooved base to fit with serrated edges of the shoulders of the channel.
Figure 15:
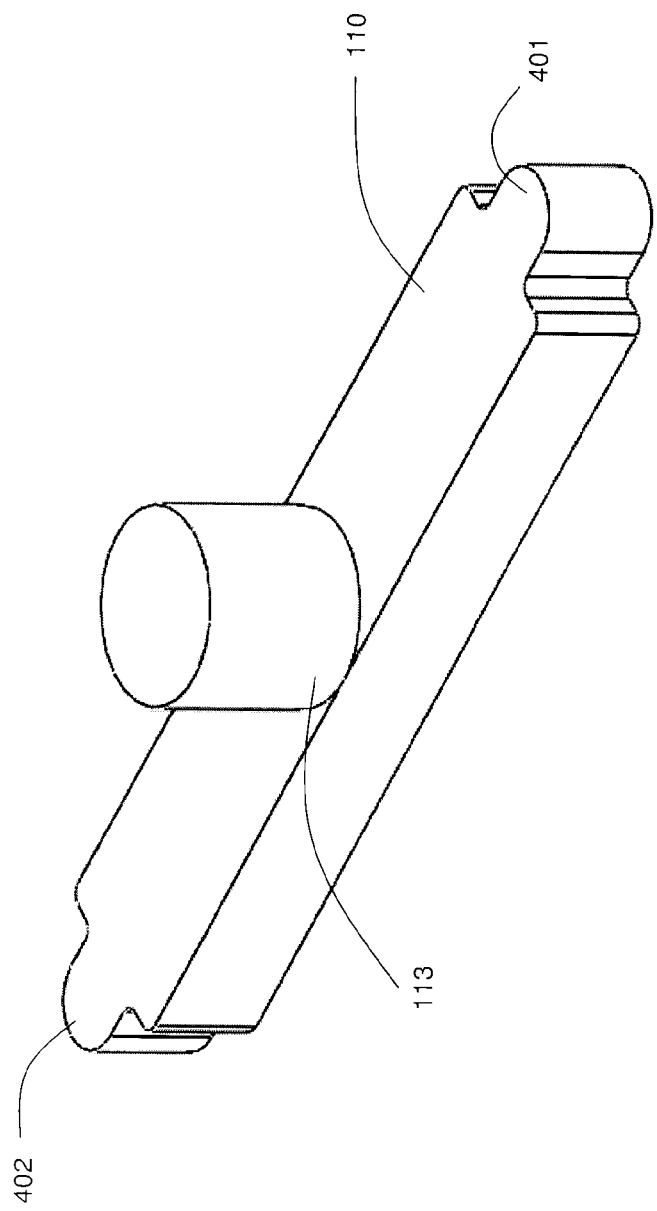
FIG. 15 is a detailed view of the grooved floss pick base.
Figure 16:
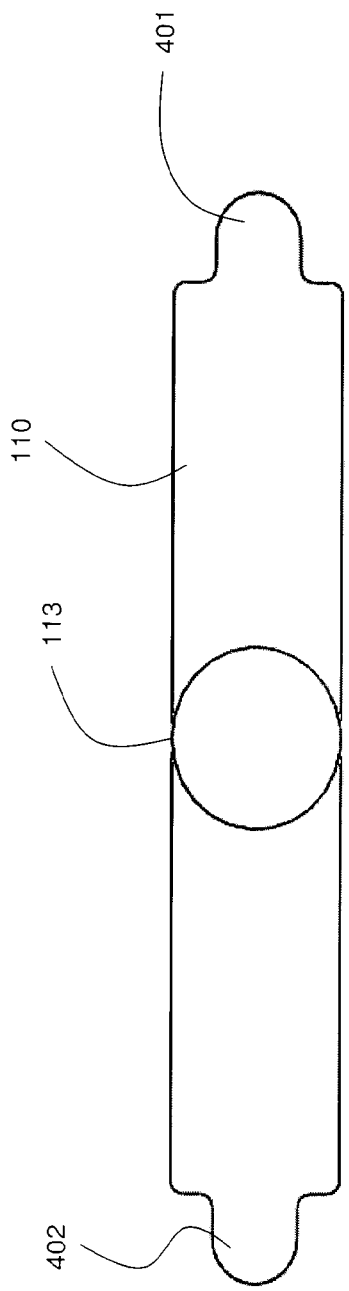
FIG. 16 is a top view of the grooved floss pick base.

FIG. 14 illustrates the floss pick 115 grooved adjustment component 401, 402 attached to the floss pick base 110. Also illustrated is the neck 113, U shaped arms 111 and floss strand 112. FIG. 15 is a detail of the grooved floss pick base 110 and neck 113 with the protrusions 401, 402 at each end of the base. These protrusions fit within serrations on the channel shoulders. FIG. 16 is a top view of the base illustrating the base 110, neck 113 and protrusions 401, 402.

Figure 17:
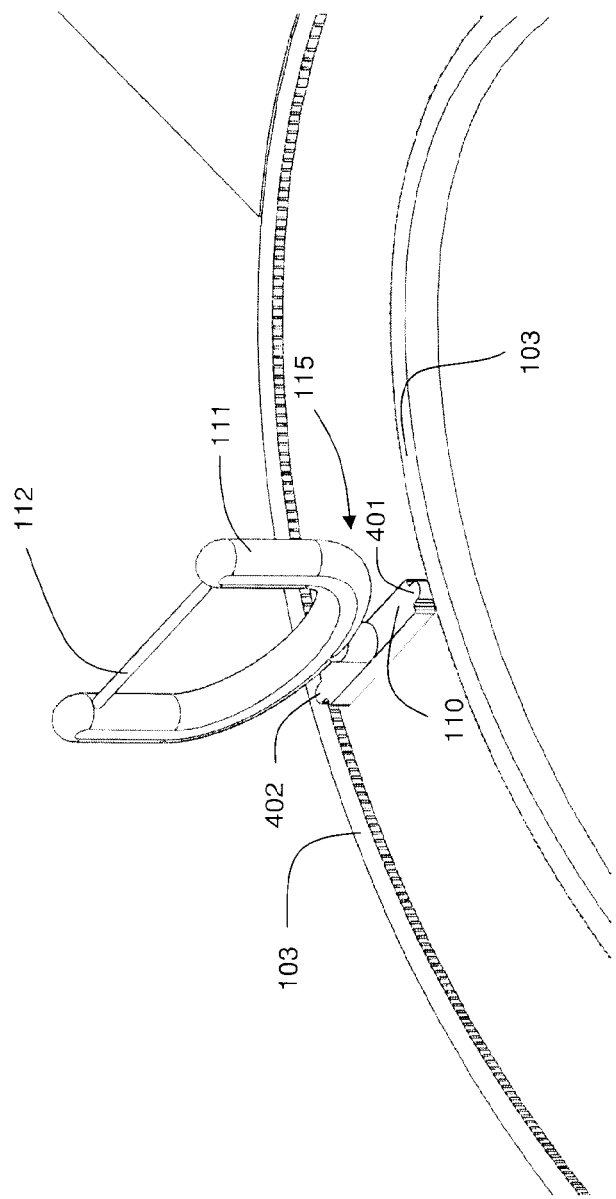
FIG. 17 is a perspective view of the serrated edge of the retainer shoulders of the channel in moveable communication with the grooved floss pick base.

FIG. 17 illustrates a perspective view of the combined floss pick 115 with the retainer shoulders 103. Also illustrated is the floss pick base 110, protrusions 401, 402, U shaped arms 111 and strand of floss 112. It will be appreciated that the shoulders 103 of the retainer may extend over the floss pick base 110 and the serrated edges or protrusions and recesses as described below.

Figure 18:
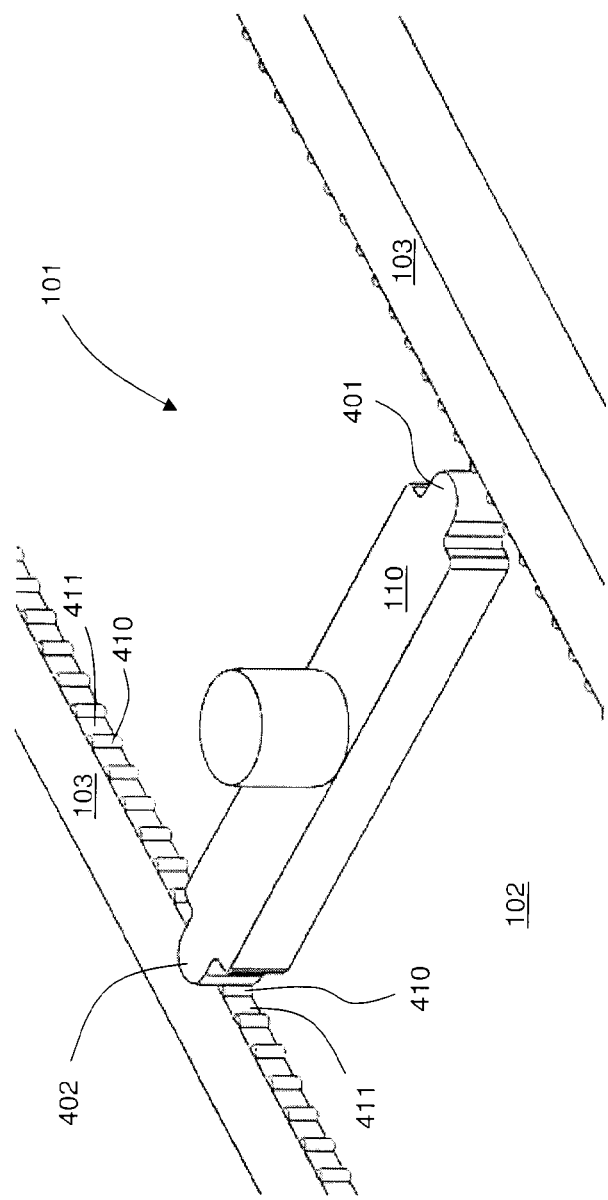
FIG. 18 is a detailed view of the components of the serrated edges that interact with the grooved floss pick base.

FIG. 18 is a detailed perspective illustration of the floss pick base 110 with the protrusions 401, 402 interfacing with the shoulder protrusions 410 and recesses 411. In one embodiment, the number of protrusions along the retainer shoulder is greatest at the location where the radius of the dental arch is smallest.

The protrusions 401, 402 of the base 110 may be made of compliant material. The shoulder 103 protrusions 410 and recesses may also be made of compliant material thereby allowing the base 110 to pass across the protrusion 410. Also illustrated is the flat bottom surface of the channel 101.

Figure 19:
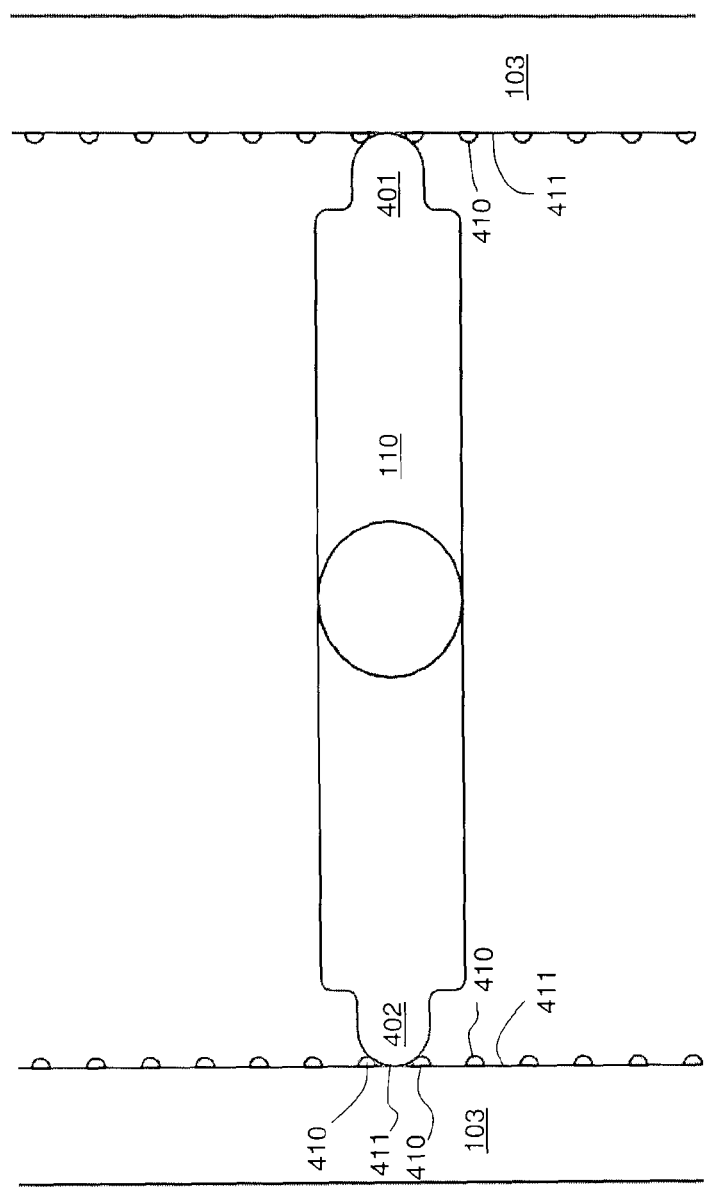
FIG. 19 is a top view of the floss pick base interacting with the components of the serrated shoulder edges of the retainer channel.

FIG. 19 comprises a top view of the floss pick base 110 with the end protrusions 401, 402. Also illustrated are the shoulders and the protrusion 410 and recesses 411.

Figure 20:
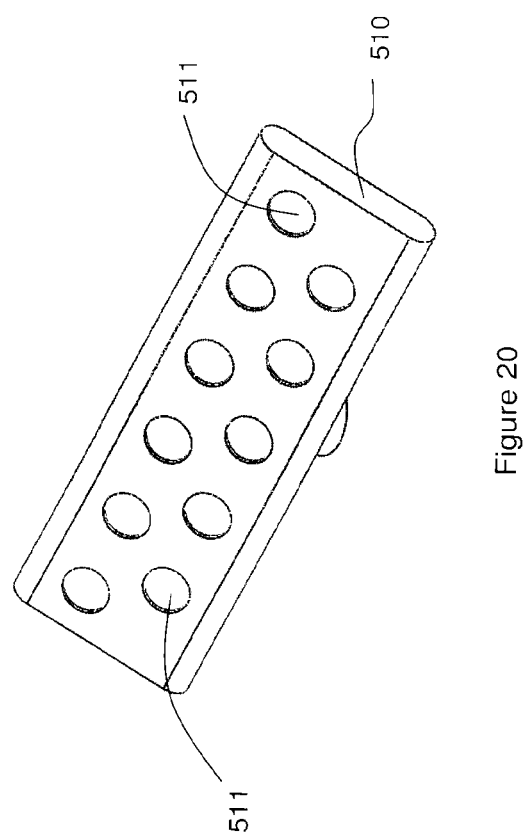
FIG. 20 illustrates a perspective view of a gel or paste applicator that comprises several perforations from which cleaning gel or paste may be applied to one floss pick or multiple floss picks simultaneously.
Figure 21:
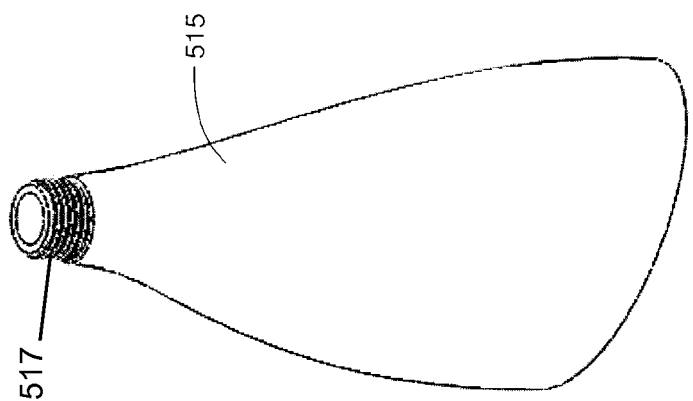
FIG. 21 illustrates a cleaning gel or paste container attachable to the paste applicator.
Figure 22:
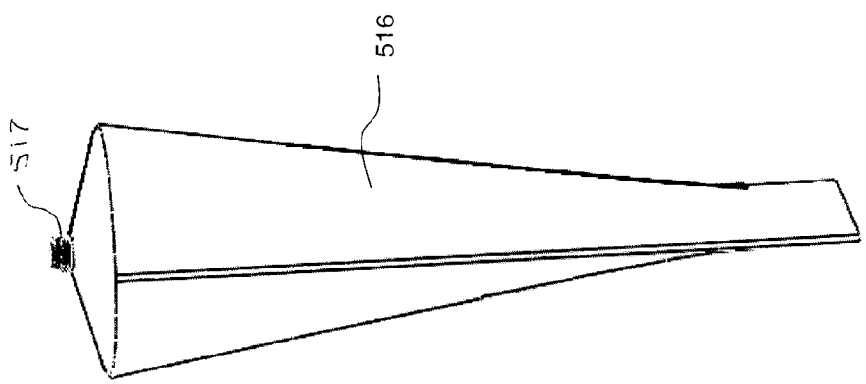
FIG. 22 illustrates a cleaning floss gel or paste tube.
Figure 23:
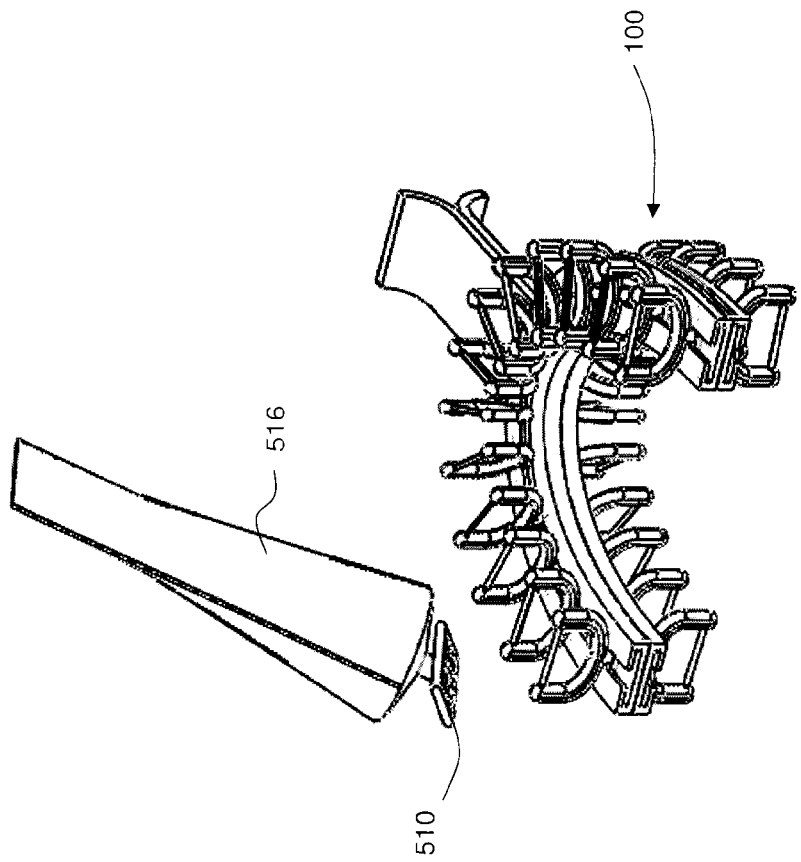
FIG. 23 illustrates a perspective view of the floss cleaning gel or paste tube with applicator and the assembled floss pick retainer.

In addition the disclosure includes an apparatus FIG. 20 to apply a toothpaste or cleaning gel to the floss of the device. The apparatus comprises an applicator 510 shaped to transfer paste or gel to the surfaces of the floss picks. The applicator may be threaded 517 onto the tube 515 illustrated in FIG. 21. The applicator may be angled to the tube axis of orientation. Additionally, the applicator may comprise a plurality of perforations 511 through which the paste or gel may be transferred to one floss pick or multiple floss picks simultaneously. FIG. 22 illustrates another embodiment of the gel or paste tube, including applicator attaching threads 517. FIG. 23 illustrates the tube and applicator in relationship to the floss pick retainer. The cleansing gel or paste may include fluoride or teeth whitening agents. The cleansing gel of paste may comprise additives found in tooth paste but may have a lower or higher viscosity to facilitate the disbursement of the cleaning gel or paste over the tooth surface and below the gum line. The fibrous floss strand, hooped strand or bristle may serve as an excellent disbursement mechanism. It will be appreciated that the device may overcome the limitations of brushing the back teeth with a toothbrush with superior disbursement of cleansing gel and antibacterial agents.

In another embodiment, the retainer can comprise sides with increased heights. The height may correspond to the gum line of the teeth. The height of the retainer sides may vary such that the sides are shorter proximate to the back teeth and higher proximate to the front teeth. The spacing between the retainer sides may also vary. For example, the spacing may be wider proximate to the back molars and more narrow proximate to the front incisors. The length of the floss strands may also vary to be longer or shorter corresponding to their intended location on the retainer. It will be appreciated that the variable retainer width above described may cause the strands of floss, held between the retainer sides, to become more slack when moved to a narrower region of the retainer. Variable retainer height and width and variable floss strand length can be advantageous in conforming to the jawline.

The shoulders of the retainer can also be modified. In this further embodiment, the shoulders are not holding the base of the floss pick. Instead, each shoulder forms a track component that holds the enlarged ends of the floss strands. Each opposing shoulder is similarly configured and holds opposite ends of the floss strands. The track components may be constructed as part of each shoulder and opposite a track contained in the opposing side of the retainer. Each track may extend along the length of the retainer and around the dental arch. The track components may be constructed of compliant material. The retainer can also be constructed of compliant material. A track may comprise a tubular shaped annulus with an opening or slot extending the length of the track. The opening can be directly opposite the opening of a second track comprising the opposing track on the second retainer side. The device can be supplied with the floss stands pre positioned in the general interproximal dental spaces. The individual floss strands may be slideably moveable in each track, thereby allowing the position of the strand traversing the retainer to be independently changed or adjusted.

Figure 24:
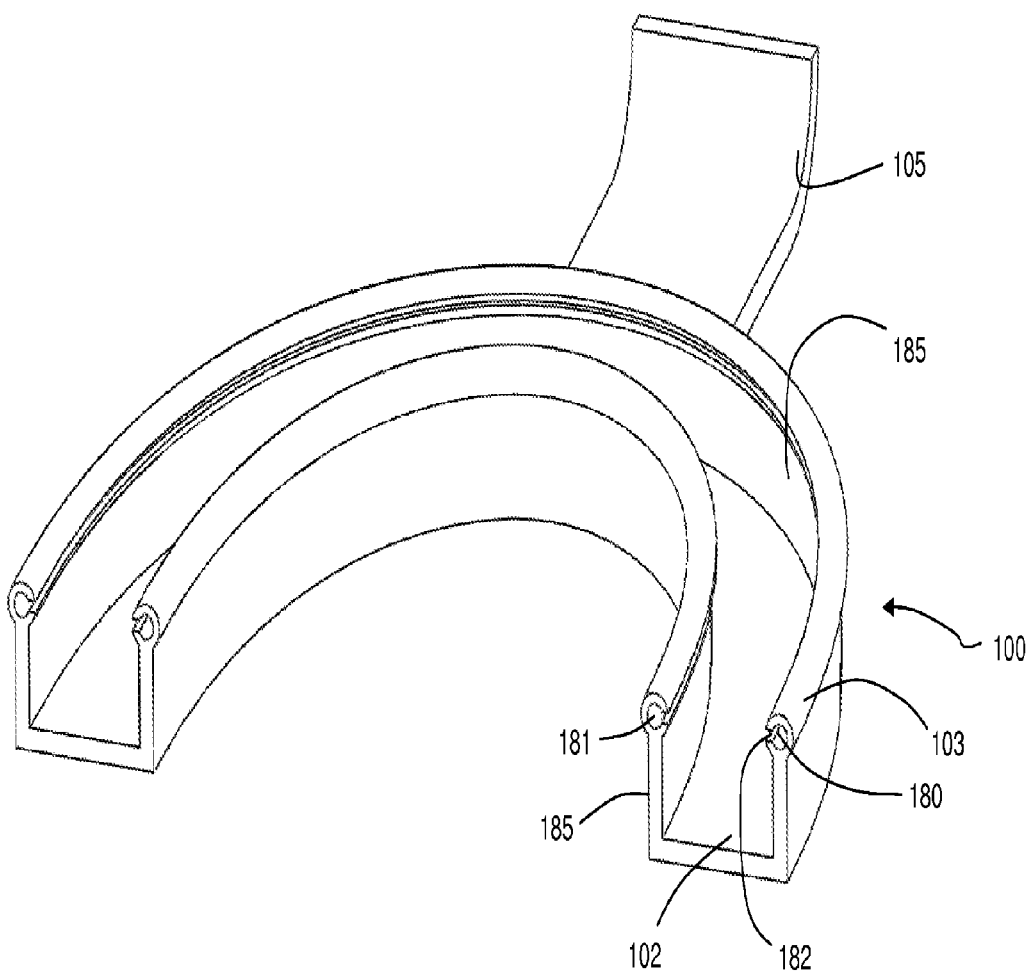
FIG. 24 illustrates a retainer further comprising shoulder components that each include a track in which floss strand ends can be inserted and wherein the floss stands traverse across the retainer.

FIG. 24 illustrates the retainer 100 of this embodiment. The retainer has an arch shape matching the dental arch. The retainer may also include a handle 105. The retainer comprises a bottom 102, sides 185, and shoulders 103. The shoulders each comprise a track 180, 181 and a slot or opening 182 that communicates with an annulus or a space between the inside of one track and the opposing retainer side and track.

The floss strand comprises two ends. The ends are enlarged and dimensioned to fit in the shoulder tracks.

Figure 25:
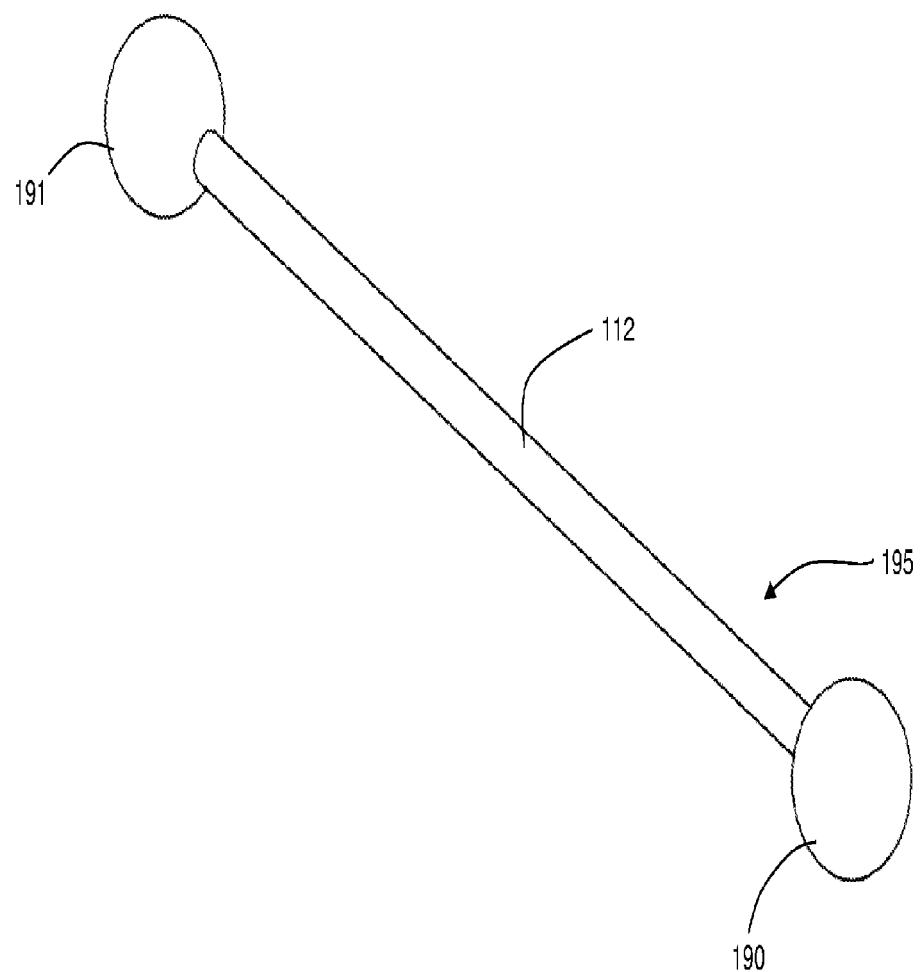
FIG. 25 illustrates a floss strand containing two enlarged end components dimensioned to fit within the retainer tracks. Between the enlarged end components is the floss strand that traverses across the retainer between the side walls.

FIG. 25 illustrates the floss strand 195 of this embodiment. Each floss strand comprises two enlarged ends 190, 191 and a floss strand 112. The floss strand may contain bristles or looped floss (not shown). The enlarged ends can be of various constructions. The ends may be knotted portions of the floss strands. The ends may be spherical or disk shaped. The floss ends are moveably adjustable in the retainer tracks.

Figure 26:
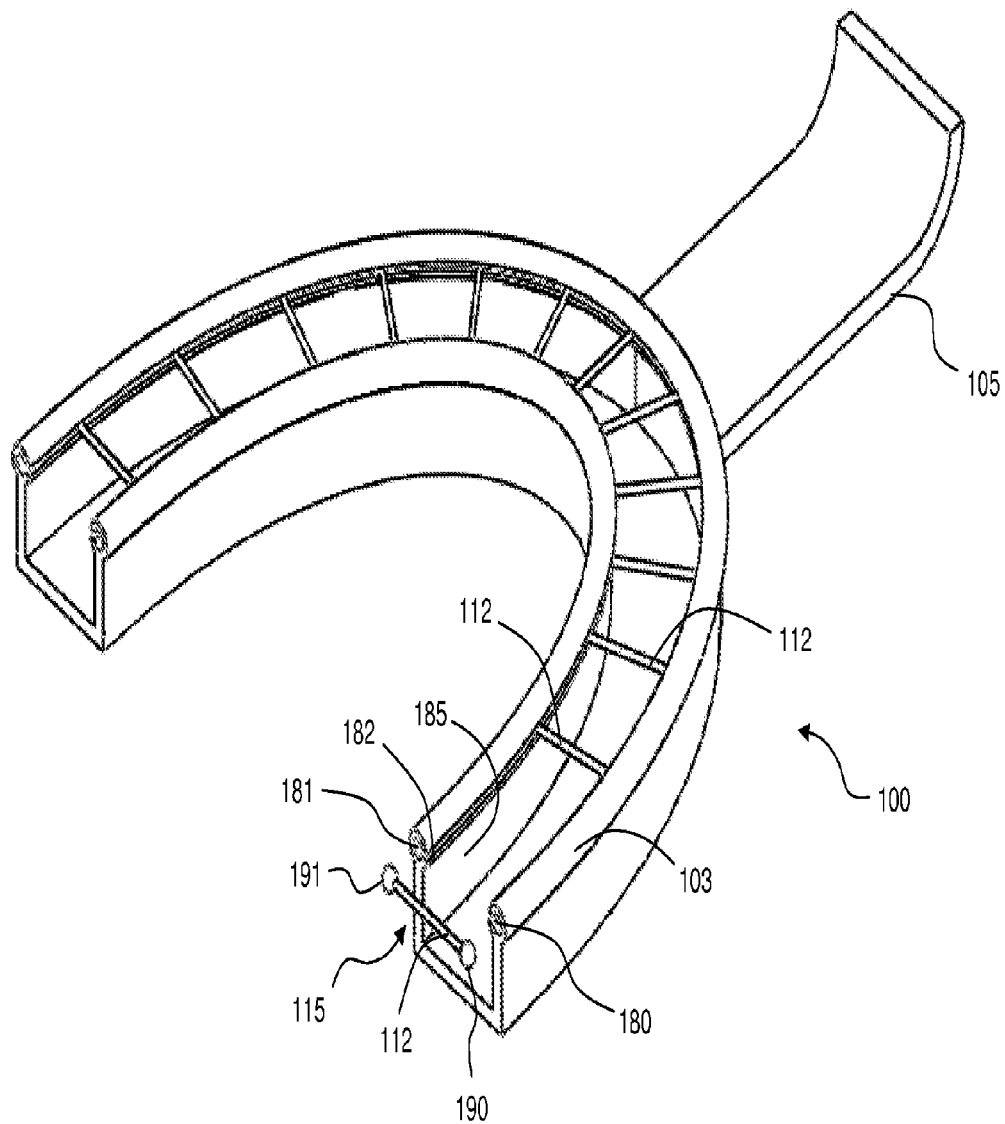
FIG. 26 illustrates a detail perspective view of the ends of the shoulder components and the track at the end of each shoulder in which the floss strand end fits such that the retainer space is traversed by the floss strand. Also illustrated is a plurality of floss strands adjustably positioned in the dual track component of the retainer.

The floss strands fit into the retainer as illustrated in FIG. 26. Illustrated is the retainer 100 with a floss strand 195. The enlarged ends 190, 191 of the floss strands are dimensioned to fit into the tracks 180, 181 of the retainer shoulders 103.

The retainer illustrated in FIG. 26 can be used in conjunction with a second inverted retainer containing floss strands for the lower jaw (not shown). This configuration is comparable to the configuration illustrated in FIGS. 6 and 7 above but using floss strands positioned on the retainer shoulders.

Figure 27:
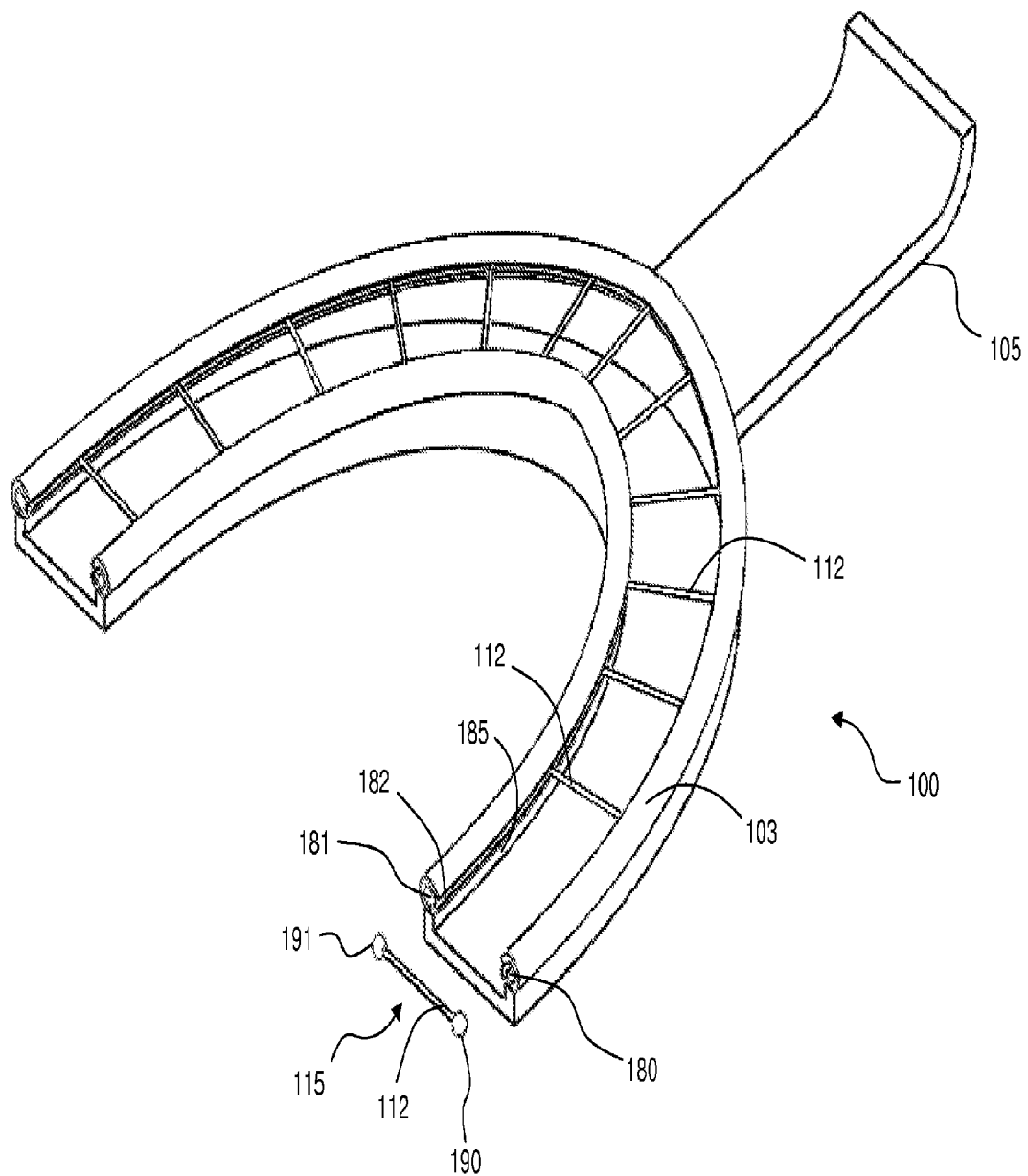
FIG. 27 illustrates a perspective view of the retainer showing the variable height of the shoulder components. The shoulder height is lower proximate to the back of the retainer and higher at the front of the arch structure proximate to the handle. The retainer tracks follow the variation in height of the shoulder components.

FIG. 27 illustrates a perspective view of the retainer 100 wherein the sides 185 of the retainer are of variable height. The sides are lower at the back of the retainer and increase in height proximate to the handle 105. Also illustrated are the tracks 180, 181 located at the top of the sides 185 forming the retainer shoulders 103. Also illustrated are floss strand components (floss picks) 115 comprising the enlarged ends 190, 191 and the floss strand 112. The enlarged ends of the floss strand component are dimensioned to fit in the tracks 180, 181 and the floss strand extends from the slot 182 of each track. It will be appreciated that the ends of the tracks may be closed on the retainer to prevent removal of the floss stands.

It will be appreciated that due to the construction of the retainer illustrated in FIG. 27 that the floss strands positioned near the front of the retainer will be positioned higher above the retainer bottom that the floss stands located at the back. (Reference FIG. 1a for an illustration of the retainer bottom 102.) This variation will accommodate the longer length of the front teeth compared to the back molars. This will allow the floss strands to reach the gum line of both the front and back teeth.

In one embodiment, the ends of the tracks are closed, thereby preventing the floss strands from being removed from the ends of the tracks.

This specification is to be construed as illustrative only and is for the purpose of teaching those skilled in the art the manner of carrying out the invention. It is to be understood that the forms of the invention herein shown and described are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention maybe utilized independently of the use of other features, all as would be apparent to one skilled in the art after having the benefit of this description of the invention.

While specific embodiments have been illustrated and described, numerous modifications are possible without departing from the spirit of the invention, and the scope of protection is only limited by the scope of the accompanying claims.

What I claim is:

1. A device for flossing teeth comprising a retainer defined by a bottom with side walls extending there from and terminating in shoulders having tracks with slots disposed along the length of the shoulders, the shoulders extending the length of the retainer, the tracks and slots being open at the ends of the shoulders, the tracks being operationally configured to retain opposing ends of one or more floss strands within the tracks, the one or more floss strands being slideably and positionally moveable in the tracks of the retainer.

2. The floss retainer device of claim 1 wherein the tracks are dimensioned to retain enlarged opposing floss ends.

3. The floss retainer device of claim 1 wherein the tracks comprise a tubular shaped annulus with a slot extending the length of the track.

4. A floss retainer device of claim 1 wherein the one or more floss strands may be independently slideably positioned proximate to interproximal dental spaces.

5. The floss retainer device of claim 1 further comprising bristles or floss hoops.

6. The floss retainer device of claim 1 wherein the one or more floss strands are independent floss strands, each positionally moveable in the tracks of the retainer through the slots.

7. The floss retainer device of claim 1 wherein the retainer is U shaped.

8. The floss retainer device of claim 7 dimensioned to conform to a dental arch of a lower jaw or upper jaw.

9. The floss retainer device of claim 3 wherein a floss strand can be placed in a first position in the tracks of the retainer and later placed in a second position in the tracks of the retainer.

10. The floss retainer device of claim 9 wherein the opposing ends of the one or more floss strands are held in position in the tracks of the retainer by friction.

11. The floss retainer device of claim 9 further comprising compliant material that holds the one or more floss strands in a moveable position.

12. The floss retainer device of claim 1 wherein the retainer side walls are spaced variably apart.

13. The floss retainer device of claim 1 wherein the retainer side walls may include a variable height.

14. The floss retainer device of claim 13 further comprising floss strands of different dimensions.

15. A method of flossing teeth comprising a) providing a retainer defined by a bottom with side walls extending there from the length of the retainer, the side walls terminating in shoulders extending the length of the retainer and having tracks with slots disposed along the length of the shoulders, the tracks and slots being open at the ends of the shoulders, b) providing a plurality of floss strands with ends dimensioned to fit in the tracks, c) positioning a plurality of floss strands on a retainer via the openings of the tracks and slots at the ends of the shoulders, and d) inserting the floss strands into an interproximal dental space.

16. The method of claim 15 comprising inserting a floss strand including bristles or hoops into the interproximal dental space.

17. The method of claim 15 comprising attaching a plurality of floss strands in opposing tracks on each shoulder of the retainer and positioning the floss strands across the retainer to align the strands with the interproximal dental spaces.

18. A method of flossing teeth comprising the steps of:
a) providing a retainer containing one or more floss strands, the retainer being defined by a bottom with side walls extending there from and terminating in shoulders having tracks with slots disposed along the length of the shoulders, the shoulders extending the length of the retainer, the tracks and slots being open at the ends of the shoulders, the tracks being operationally configured to retain opposing ends of the floss strands within the tracks;
b) moving one or more floss strands within the tracks in relation to the retainer;

c) placing the retainer in a user's mouth; and
d) closing the user's mouth on the retainer to position the one or more floss strands in corresponding interproximal dental spaces.

19. The method of claim 18 further comprising inserting the one or more floss strands into the tracks via the openings at the end of the shoulders and moving the one or more floss strands in relation to the retainer to match the user's interproximal dental space.

20. A floss strand retainer device including a first retainer for the upper jaw and a second inverted retainer for the lower jaw; each retainer being defined by a bottom with side walls extending there from and terminating in shoulders having tracks with slots disposed along the length of the shoulders, the shoulders extending the length of the retainers, the tracks and slots being open at the ends of the shoulders, the tracks being operationally configured to retain opposing ends of one or more floss strands within the tracks, wherein the opposing ends of the one or more floss strands have enlarged opposing ends independently and slideably, positionally moveable within the tracks.

* * * * *